United States Patent
McCulloch et al.

(10) Patent No.: US 9,532,905 B2
(45) Date of Patent: Jan. 3, 2017

(54) GOGGLE WITH BATTERY PODS

(71) Applicant: Abominable Labs, LLC, Lake Oswego, OR (US)

(72) Inventors: David McCulloch, Lake Oswego, OR (US); Jack Cornelius, Lake Oswego, OR (US); Toren Orzeck, Portland, OR (US)

(73) Assignee: Abominable Labs, LLC, Lake Oswego, OR (US)

( * ) Notice: Subject to any disclaimer, the term of this patent is extended or adjusted under 35 U.S.C. 154(b) by 139 days.

(21) Appl. No.: 14/433,378

(22) PCT Filed: Oct. 29, 2013

(86) PCT No.: PCT/US2013/067308
§ 371 (c)(1),
(2) Date: Apr. 2, 2015

(87) PCT Pub. No.: WO2014/070770
PCT Pub. Date: May 8, 2014

(65) Prior Publication Data
US 2015/0290039 A1    Oct. 15, 2015

Related U.S. Application Data

(60) Provisional application No. 61/721,047, filed on Nov. 1, 2012, provisional application No. 61/750,644, filed on Jan. 9, 2013.

(51) Int. Cl.
*A61F 9/02* (2006.01)
*A42B 3/24* (2006.01)
(Continued)

(52) U.S. Cl.
CPC .......... *A61F 9/029* (2013.01); *A42B 3/24* (2013.01); *A42B 3/245* (2013.01); *H01M 2/1005* (2013.01);
(Continued)

(58) Field of Classification Search
CPC ............ A61F 9/029; A42B 3/24; A42B 3/26; A42B 3/245; H01M 2/1005; G02C 11/10
See application file for complete search history.

(56) References Cited

U.S. PATENT DOCUMENTS 2,207,705 A    7/1940  Cox
6,047,411 A *  4/2000  Ryden .................... A61F 9/028
                                                    2/171.3

(Continued)

*Primary Examiner* — Katherine Moran
(74) *Attorney, Agent, or Firm* — Howard Russell

(57) ABSTRACT

A goggle adapted for utilizing a plurality of batteries to perform a powered function for the goggle comprising: a lens retained in a goggle body, strap extension members connected to the goggle body, each extension member defining therein a cavity having a contact for retaining a battery pod, each battery pod having a chemical cell battery therein, for powering the goggle to enable one or more of heating the goggle lens, video capture, GPS, stereo sound or other electronic function of the goggle. The cavities are symmetrical about a z-axis and the batteries for the system are interchangeable such that any battery pod may be flipped about the z-axis and retained in any battery cavity. The goggle is further comprised of a strap portion, either attached to the extension members or integral therewith, for retaining the goggle on a user's head or helmet.

16 Claims, 12 Drawing Sheets

(51) Int. Cl.
*H01M 2/10* (2006.01)
*H01M 10/42* (2006.01)
*G02C 11/00* (2006.01)

(52) U.S. Cl.
CPC .......... *H01M 10/4257* (2013.01); *G02C 11/10* (2013.01); *H01M 2220/30* (2013.01)

(56) References Cited

U.S. PATENT DOCUMENTS

| | | |
|---|---|---|
| 6,701,537 B1 | 3/2004 | Stamp |
| 7,603,078 B2 | 10/2009 | Buskop |
| 7,786,424 B2 | 8/2010 | Durner et al. |
| 9,301,879 B2 * | 4/2016 | McCulloch ............. A61F 9/025 |
| 9,351,880 B2 * | 5/2016 | McCulloch ............. A61F 9/025 |
| 2009/0151057 A1 | 6/2009 | Lebel et al. |
| 2009/0256978 A1 | 10/2009 | Park et al. |
| 2009/0307828 A1 | 12/2009 | Ludlow |
| 2012/0075167 A1 | 3/2012 | Lahcanski et al. |
| 2012/0262667 A1 | 10/2012 | Willey |
| 2013/0091623 A1 * | 4/2013 | McCulloch ............. A61F 9/025 2/435 |

* cited by examiner

GOGGLE WITH BATTERY PODS

CROSS REFERENCE TO RELATED APPLICATIONS

This patent application claims the benefit and priority of U.S. Provisional Patent Application Ser. No. 61/721,047 filed Nov. 1, 2012 and U.S. Provisional Patent Application Ser. No. 61/750,644 filed Jan. 9, 2013.

FIELD

This invention relates generally to battery-powered goggles and more particularly to a battery-powered goggle adapted for carrying batteries on the goggle strap.

BACKGROUND

Goggle Construction Generally

Sport goggles, such as are often used for skiing, cycling, snow-boarding, motorcycle and ATV riding, paint-balling, or standard-issue military goggles used primarily for military ground operations, typically have comprised a plastic frame or body and a clear plastic, or polycarbonate, see-through lens positioned as a see through screen for the user's eyes. At the ends of the goggle body there traditionally has been connected a textile, elongated, adjustable, elastic strap for holding the goggle body on a user's head or helmet by stretching the strap around the back of the head, or helmet, with the goggle positioned in opposing fashion on the face of the user.

The Need for Battery Power in Goggles

Many of today's goggles have incorporated therein such things as music playing capability, as shown in U.S. Pat. No. 7,603,078, to Buskop for Ski Goggles With Digital Music Player; video capture capability, as shown in US Patent Application No. US 2009/0307828 A1, to Ludlow, for Goggle With Built-in Camera, GPS with LCD display for buddy tracking, speed and navigation purposes, as provided in a mod adapter for standard goggles by Recon Instruments, Inc.; electronic lighting and darkening of goggle lenses as taught in US Patent Application 2009/0256978 A1, to Park et al., for Liquid-Crystal Ski Goggles And Method of Manufacturing the Same; Heads-up display technology for goggles as shown in U.S. Pat. No. 8,212,859 B2, to Tang et al., for Peripheral Treatment For Heat-Mounted Displays; and even for aiming a hand-held weapon, as shown in U.S. Pat. No. 5,379,140 to Michel et al. for Goggles Having Micro-lenses and Display Helmet. Of course, each of these electronic functions in goggles requires power for them to operate. A preferred method of powering such functions has been DC, chemical battery cell (e.g., Lithium Ion) power retained on the goggle or goggle strap.

The Need for Fog Prevention in Goggles

Fogging of goggle lenses is a very common problem with sports and military standard issue goggles. Fogging of goggles often occurs in various situations involving temperature extremes, particularly when warmer air caused by perspiration and respiration enters within a goggle enclosure and which is warmer relative to colder temperature conditions outside of the goggle body. Of course this problem has ranged from being annoying to the user, to presenting a very dangerous situation where the user's field of vision has been greatly diminished. The problem of fogged goggles has resulted in injury and even death among goggle users.

Early goggles have used passive air-flow systems, such as venting, to attempt to maintain goggle lenses fog free. Because these systems have been somewhat ineffective in preventing fogging, especially in more extreme conditions, there have been developed battery-powered, active air-flow systems, such as U.S. Pat. No. 4,150,443, to McNeilly for Anti-Fogging Sports Goggle. In McNeilly, there is disclosed a power pack for holding a nine-volt battery for powering a ventilation fan. The power pack is shown carried between two parts of the strap on one side of the body of the goggle. The battery power pack has two slots on either end of the power pack for interconnecting with the goggle strap sections.

Responsive to the limitations of passive air-flow anti-fog systems, there have also been disclosed battery-powered, resistive-element heating systems for heating of the inner surface of the lens of a goggle to prevent fogging. Heating the lens of a goggle has required more battery power than operating a ventilation fan. An example of apparatus for heating the lens of a goggle has been disclosed in U.S. Pat. No. 4,868,929, to Curcio, for Electrically Heated Ski Goggles. Curcio teaches carrying of the battery and switch in a housing on a belt of the user. One drawback of such as system is that it is cumbersome to have wiring running from the housing on the user's belt to the goggle lens.

Accordingly, another example of an apparatus for heating the lens of a goggle has been disclosed in US Patent Application Publication No. 2009/0151057 to Lebel et al., for Reversible Strap-Mounting clips for Goggles. In Lebel et al., a battery-powered lens heating system is disclosed comprising in relevant part a battery pack holder that contains a battery and which mounts the battery onto the strap via a connector. The battery pack holder includes spring loaded contacts, a positive contact and a negative contact, that are wired internal of the holder to be electrically connected to the positive and negative terminals of the battery. The holder comprises a clasp portion that is hinged to a base portion of the battery holder allowing closing of the clasp to physically and electrically interconnect the battery to contacts on the outside of the strap.

One problem of such a device as disclosed in Lebel et al. is that, being on the outside of the strap, it relies on the strength and integrity of the clasp to hold the battery and battery holder in physical and electrical contact on the strap. Should the holder/connector combination become knocked, for example during a fall, or otherwise impacted during storage and/or handling of the device, the connection could become less secure and thus less effective. Also, in this regard, the hinged mechanism relies on a movable part that is vulnerable to wear or physical impact that could weaken the connection. Further, to the degree the strap between the battery and the goggle is flexible, running of wires through it to the contact leads for interconnecting with the battery would be problematic from a wear standpoint, since the wires wouldn't be as flexible as the strap material. Still further, the holder and connector are connected on the outside of the strap where moisture can have greater access to the holder, thus placing a premium on sealing of the holder and the connectors. This system of interconnection of the battery is not provided with sufficient styling consideration so as to blend more imperceptibly with the contours of the strap, but it also does not provide a more fool-proof guide for accurately attaching the battery onto the strap. Still further, since the advent of Lebel et al., battery technology has developed significantly, and more powerful, longer lasting batteries have been provided as means for significantly enhancing the potential for battery-powered lens heating systems.

The Need for Increased Battery Power in Goggles

While the latter resistive-element heating systems have been the most effective means of preventing fogging of goggles, they have also required more significant battery power to operate for an entire day of activity. Thus, goggles have required increasing amounts of power to allow mobile functioning of electronics devices within the goggles. While electronics utilized for visual displays, playing music, GPS systems, cameras and the like have been able to function for sufficiently long periods of time with a single lithium-ion, lithium-poly, nickel-cadmium or other chemical battery cell able to be carried on a goggle strap, the power requirements for longer-term prevention of fogging of goggle lenses for extended activity periods have been greater, thus necessitating multiple batteries, which have not been able to be conveniently carried on a single strap.

The capability of a single rechargeable chemical battery cell is to produce a maximum voltage in the range of 1.2 to 4.2 volts. However, goggle de-fogging heating elements, which have presented low-resistance to the power supply on the order of 5-10 ohms, have required higher voltage than a single battery cell can conveniently produce to operate in an efficient range. Combining two such batteries in a serial configuration, the available voltage of the entire power supply becomes equal to the total voltage of each single supply added to each other. For instance, if a single battery produces four volts, two such batteries in series produce about eight volts. By operating batteries in a serial configuration one can meet the voltage requirements necessary for modern transparent, low-resistance heating elements to prevent fogging.

Thus, goggle lens heating operations have consumed a substantial amount of battery power relative to readily and conveniently wearable battery power storage means. Accordingly, a problem with prior art battery systems for powering goggles has been that there has not been sufficient battery power that is convenient to wear on the goggles, or on the strap of the goggles, for example to keep the goggle lens heated during a sufficient amount of time to allow a day of fog-free activity. Part of the reason for this has involved the fact that adequate such battery power has been too heavy to comfortably wear on the strap or in the goggle itself. And this, in turn, is in part because commonly used textile straps have not been sufficiently rigid to hold the heavier batteries required.

Accordingly, a system for plugging goggles into a vehicle battery, such as for a snowmobile, has been developed as shown in U.S. Pat. No. 4,638,728, to Elenewski, for Visor Defroster. Drawbacks to such a system are that not all activities involve the use of a vehicle, and more problematic is the need for a tethering type wiring system extending from the vehicle to the visor, or goggle.

Another part of the reason for the lack of sufficient convenient battery power for goggle lens heating has been that more powerful lithium-ion type batteries have not been as readily available for consumer use until more recently with the advent of modern cellular telephone usage.

There has developed a need for a system of easily storing, securing, and quickly and efficiently installing battery power for a goggle to avoid lens fogging and/or for other goggle power. Further, there has developed a need for an improved, aesthetically pleasing system for conveniently and securely providing substantial and consistent battery power to a goggle. Such a system would not only be aesthetically pleasing to the eye, but would be designed to be convenient to use, convenient to recharge, simple to change batteries in the field for fresh, readily storable backup batteries carried elsewhere, such as in a fanny pack or on a bandolier, on the user. Such a system would also be highly effective in securely attaching the battery to the goggle strap in such a way that the system could withstand impacts associated with the physical activities during which such goggles are commonly worn.

SUMMARY

In accordance with a first aspect of the invention, there is provided a battery-powered goggle capable of performing a powered function within the goggle. The goggle comprises a goggle body having wiring therein and first and second ends. There is also provided a goggle lens retained within the goggle body. Connected to the goggle body there are provided first and second extension members. Each extension member has a first end, a second end, an inner surface and an outer surface. The first end of each extension member is connected with respective first and second ends of the goggle body. In other words, the first end of the first extension member is connected with the first end of the goggle body, and the first end of the second extension member is connected with the second end of the goggle body. Each extension member has wiring in the extension member connected to the wiring in the goggle body for interconnecting a battery to the wiring in the goggle body. Each said extension member defines at least one concave molded cavity open to one of the inner surface of the extension member and the outer surface of the extension member. Within each cavity there are contacts for interconnecting the battery to the wiring in the extension member. The goggle further comprises a strap portion having first and second ends, the first end of the strap portion being connected with the second end of the first extension member and the second end of the strap portion being connected with the second end of the second extension member. The goggle further comprises a plurality of batteries and a plurality of battery pods, each battery pod comprising a container containing or holding at least one battery, each battery pod being adapted for being releasably retained in any cavity of any extension member. In other words, each cavity of each extension member retains a battery-containing pod during use, and each battery pod may be removed from its corresponding cavity. Each battery pod is further adapted for providing a contact between the battery in the container of the battery pod and the contact within each cavity of each extension member. Thus, this inwardly opening cavity and pod combination yields a goggle system that is enabled for transmission of power from the batteries to power the goggle in a system that is both functional and aesthetically pleasing to the eye.

In accordance with another aspect of the invention, there is provided a dual-battery-pod powered goggle capable of heating the lens of the goggle. The goggle in accordance with this aspect of the invention comprises a goggle body having wiring therein and first and second ends and a lens retained within the goggle body, the lens having a resistive heating element thereon interconnected with the wiring in the goggle body. The goggle further comprises first and second extension members integrally connected to the goggle body, each of the extension members having a first end, a second end, an inner surface and an outer surface, each of the extension members having wiring therein connected to the wiring in the goggle body for interconnecting a battery to the wiring in the goggle body. Further, each extension member defines at least one concave molded cavity open to the inner surface of the extension member and having defined within the cavity contacts to enable interconnecting of the battery to the wiring in the extension member. The first end of each extension member is integrally connected with respective first and second ends of the goggle body. Thus, in accordance with this aspect of the invention, the first end of the first extension member is integrally connected with the first end of the goggle body, and the first end of the second extension member is integrally connected with the second end of the goggle body. The goggle in accordance with this aspect of the invention further comprises a strap portion having first and second ends, the first end of the strap portion being connected with the second end of the first extension member and the second end of the strap portion being connected with the second end of the second extension member. The goggle further comprises a plurality of batteries and two (that is first and second) battery pods. Each battery pod comprises a container containing at least one of the batteries and is adapted for being releasably retained in any cavity of the extension members. Each battery pod is adapted for providing a contact, or contacts, between the battery in the container and the contacts within any cavity of any extension member. Thus, the goggle in accordance with this aspect of the invention is enabled in providing transmission of power from the batteries to heat the goggle lens.

Preferably, the extension members of either aspect of the invention are comprised of thermal plastic polyurethane (TPU) or silicone rubber that is semi-flexible in lateral and transverse directions, but somewhat resistant to stretching in a longitudinal direction. Further, preferably, each such extension member and at least a portion of the goggle body are made of contiguous, integral thermal plastic polyurethane (TPU) or silicone. Also, with either aspect of the invention, the strap portion may be comprised of a textile strap that is sewn or otherwise attached to the silicone extension member, or alternatively, the strap may be comprised of a likewise integral piece of silicone. Still further, preferably, the extension members of the goggle of any of the foregoing aspects of the invention each further define a channel for the wiring to be retained within the extension member. Such channel preferably communicates with a corresponding channel preferably formed within the goggle body for retaining wiring for connecting with the heating element of the lens or other goggle electronics.

In accordance with another aspect of the invention, and together with any of the foregoing aspects of the invention, each battery, battery pod and cavity contact of the goggle further comprises a pair of contacts comprising a positive polarity contact and a negative polarity contact, and each cavity and pair of cavity contacts are located in a corresponding extension member, each cavity and pair of cavity contacts being located substantially symmetrically about a transverse y-z plane cutting vertically through the bridge of the nose of the goggle body, with two symmetric lateral halves of the lens and goggle body extending substantially symmetrically outwardly from the plane to their ends, and with an extension member substantially symmetrically positioned on each side of the plane. Preferably, each cavity and cavity contact is located in a corresponding extension member, and is located substantially symmetrically about, that is on either side of, the transverse y-z plane passing through the goggle body and oriented so that each cavity opens to the inside surface of each extension member. This allows that each battery pod is the same, or identical, and capable of being releasably retained in any one of the cavities in any extension member. Thus, there is enabled and provided that a single type of battery pod may be used in each cavity on either extension member, and preferably the positive and negative battery pod contacts of each battery pod are each oriented symmetrically about the transverse plane and connected with the positive and negative contacts of each cavity such that the battery contacts and the cavity contacts are also located in a anterior portion of each cavity that is closest to the goggle body. This requires that the wiring of the goggle is made using a serial connection of the batteries where the cavity contact poles, and hence the battery pod contact poles when installed in the cavities, are symmetrically reversed in polarity relative to each other about the aforementioned transverse plane through the goggle body. That is, for example, while the positive poles of each cavity and battery pod may be oriented closer to the transverse plane, the negative poles of each cavity and battery pod will be further from the transverse plane, or vice-versa, to enable use of a single type of battery pod in symmetrical fashion about the transverse y-z plane in each inwardly-opening (or alternatively outwardly-opening) cavity in each extension member. This, in turn enables use of the same type of battery pod, which is rotated 180 degrees about the z-axis so as to be symmetrical on each side of the y-z plane, depending upon which extension member/strap portion of the goggle in which the battery pod is installed.

These aspects of the invention enable convenient carrying of sufficient chemical battery cells on the goggle, or strap, to power a lens heating operation, and/or other electronic operations, for an entire day of skiing, e.g., for eight hours, without any need for recharging the batteries.

Further, these aspects of the invention simplify the process of carrying backup replacement batteries for installation in the goggle, since the same type of battery pod may be used on either side of the goggle without sacrificing aesthetic symmetry of the goggle. This, in turn makes it easier to store in reserve and carry a plurality of backup battery pods able to be used in symmetrical fashion on either side of the goggle body, since a user only has to be concerned about one type of battery pod, and these additional reserve battery pods may be stored on one of a user's body and a bandolier. The batteries may be charged while in their pods either through a charging jack on the goggle itself, or in a charging base external of the goggle. Also, each said battery pod preferably further comprises integrated means protecting against short circuit, over-voltage from the charger, under-voltage from the charger, over-temperature and current limitation circuitry, all to protect against harm to the user or damage to the battery or the goggle.

In accordance with another aspect of the invention, each battery pod and cavity further comprises a spring-biased, thumb-releasable, tongue-and-groove interconnection means for securely, but releasably, interconnecting the battery pod in the cavity. This aspect of the invention provides for easy latching and secure attachment replacement of battery pods into a battery pod cavity or receptacle, together with easy thumb release of pods, overcoming a spring bias for installing and removing the battery pods from their battery pod cavities. This in turn makes the invention easy to use in the field, while climbing, hiking or on the slopes, and whether or not the user is wearing gloves.

DESCRIPTION OF EMBODIMENTS

Figure 1:
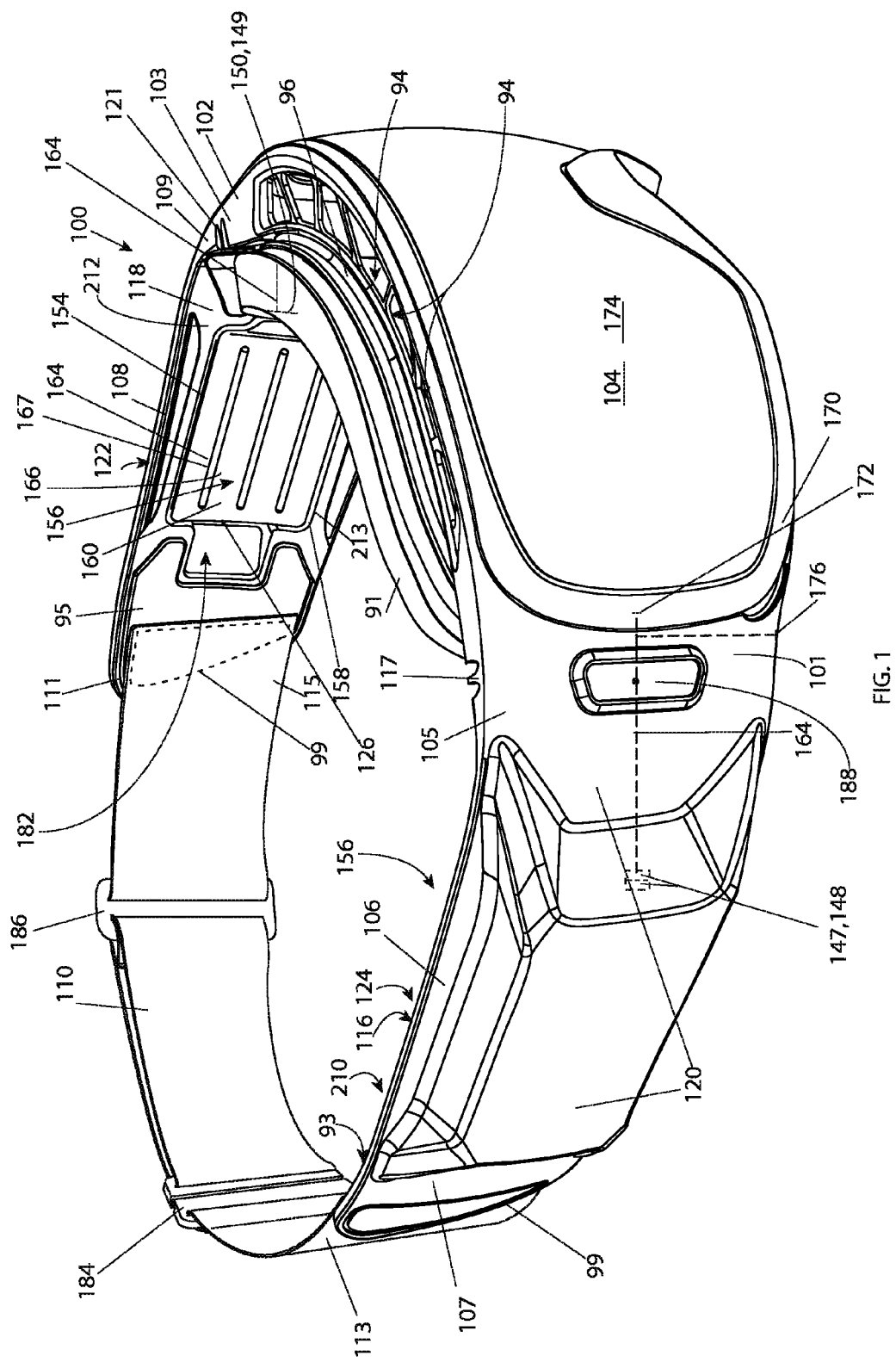
FIG. 1 is a left front perspective view of a battery-powered goggle in accordance with an embodiment of the invention having battery pods installed in strap portions (i.e., goggle body extension member portions) of a goggle.

Referring to FIGS. 1-3, 5, 8 and 10, there are shown components for an embodiment of a goggle 100 that comprises a multi-pod, symmetrically-balanced, goggle-strap-mounted power supply system. The goggle 100 comprises a body 102 having ends 101, 103, a lens 104 installed in the body, a plurality of body extension members 106, 108 and an elastic, stretchy, textile strap portion 110 having ends 113, 115. The goggle 100 also preferably comprises a flexible, spongy, foam interface peripheral member 91 attached around a posterior periphery 96 of the goggle body 102. The foam interface member 91 is for interfacing with the use's face and the semi-rigid, lightweight plastic, or other suitable material, such as silicone, posterior portion 96 of the anterior goggle body 102 for interfacing with the lens 104. The posterior flexible and spongy portion 91 of the body 102 engages the user's face around the user's eyes and on the bridge of the user's nose at 97, while the anterior periphery member 103 provides a base or foundation upon which the lens 104 is engaged. Further, the goggle body 102 may be provided with conventional ventilation ports 94 in the anterior portion 103 of the goggle body.

Incorporation by reference is made herein to U.S. patent application Ser. No. 13/587,908, for Goggle with Easily Interchangeable Lens that is Adaptable for Heating to Prevent Fogging, to McCulloch et al., wherein an interchangeable series of lenses are shown and described having varying types of resistive element, or resistive film, heating elements thereon, or alternatively having no heating element on the lens at all without departing from the scope and spirit of the invention, the goggle of the present application likewise employing similar lens types. In the case where there is no lens heating operation involved, the battery pods 156 and batteries 159 would be useful to power other electronic functions of the goggle 100, such as GPS, video, sound, heads-up display, and other electronic functions. As described in the Ser. No. 13/587,908 application to McCulloch et al., the lens 104 of the present invention is preferably easily interchangeable as shown and described in that patent application. The lens 104 may be a clear lens, or a tinted lens as known in the art, the lens preferably having a clear anti-fog resistive coating 174 on an inner surface of the lens, the coating further being protected with a protective layer, or double-lens construction, to protect the anti-fog surface from being scratched off. The anti-fog resistive coating 174 preferably comprises an Indium Tin Oxide (ITO) compound that may be sprayed, deposited with a known ion-sputtering technique, painted or otherwise layered or applied. The film heating member 174 may be comprised of another material designed in the form of a resistive element that generates heat when connected to an electrical circuit without departing from the true scope and spirit of the invention.

The goggle 100 further comprises a lens frame, or bezel 170, upon which the lens 104 is retained, as for example with adhesive, and the bezel further comprises engagement, e.g., a tongue and groove engagement means, or cap and ridge engagement means as described in the aforementioned patent application to McCulloch et al. Still further, the lens 104/bezel 170 comprises interconnection means, for example snaps, hooks, silicone nubs or latches, both operative to engage and secure connection with a lens contact portion 172, if any, of the goggle 100, for interconnecting a heating element portion 174 on the inner surface of the lens 104 with the batteries 159.

Since the lens 104 is easily interchangeable, a user may have multiple such lens 104/bezel 170 combinations, each such lens comprising alternate tinted lens surfaces of varying colors and/or degree of tint, again either with or without anti-fog resistive coating thereon. This feature provides that either anti-fog or non-anti-fog lenses may be used with the goggle 100 of the invention without damaging the system or even reducing battery life. This is because the electrical system of the goggle 100 is preferably a low-power system which enables safe usage of the goggle with a heated lens 104, or with a non-heated lens 104, in the goggle. This feature makes use of the goggle more care-free and flexible, as whether the battery is in use, or not, the user is encouraged in choosing a goggle 100 that suits the weather, terrain, and lighting conditions of the moment.

The body extension member 106 comprises first and second ends, 105, 107 and inner and outer surfaces 93 and 120, respectively. The body extension member 108 comprises first and second ends 109, 111 and inner and outer surfaces 95 and 122, respectively. The body extension members 106, 108 comprise in part what would otherwise be side portions of a strap of a conventional goggle. In other words, the body extension members 106, 108 are in the same location relative to a user's head as would the side portions of a strap of a conventional goggle. The first end 105, 109 of each body extension member 106, 108 extends from a corresponding end 101, 103, respectively, of the goggle body 102. As shown, accordion-type, serpentine, reticulation channel means 117, 121 may be employed between the goggle body 102 and each body extension member 106, 108, respectively, in order to ensure sufficient flexibility to the strap-type function of each body extension member to enable easy adaptation of the goggle to differently-shaped users and their various head and helmet shapes and sizes. The second end 107, 111 of each body extension member 106, 108 is attached to corresponding ends 113, 115, respectively, of the textile strap portion 110 of the strap (comprised of each extension member 106, 108 and the textile portion 110). Such attachment may be accomplished by looping the ends 113, 115 of the strap 110 around pins (not shown) embedded into the second ends 107, 111 of the body extension members 106, 108, or other means of interconnecting such dissimilar elements known in the art, such as by stitching 99.

Figure 5:
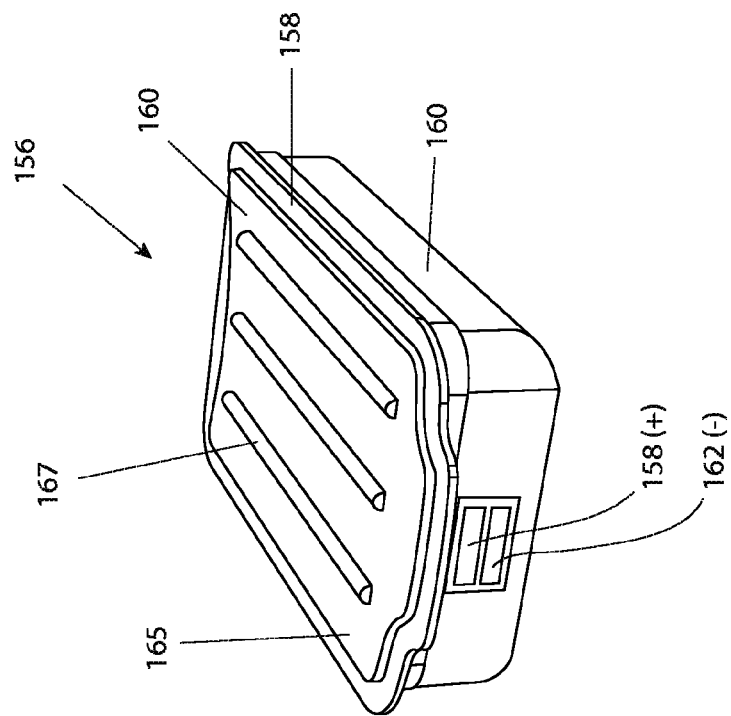
FIG. 5 is a perspective view of a battery pod and a partial battery pod having an upper containing portion removed to show the battery within the pod, both in accordance with a portion of the invention.
Figure 5:
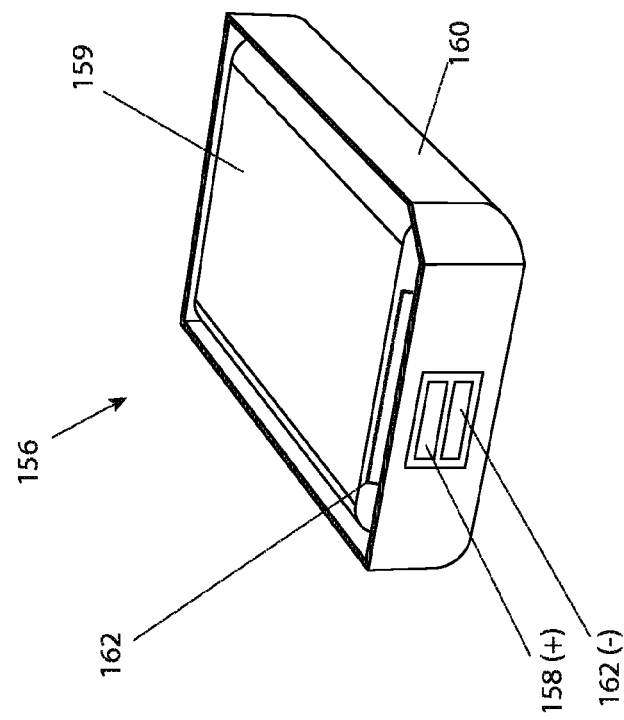

The goggle 100 further comprises a plurality of battery pods 156. Each battery pod 156 comprises a container 160 that is sealed around the battery 159 inside. An upper surface 166 of the battery pod 156 may have ribs 167 thereon to enable easier gripping of the battery pod and to also provide gripping of the pod to a user's helmet, cap or head, in the case where the container 160 may be made of hard plastic, but the ribs 167 may be made of silicone that is capable of gripping and conforming more easily to a slightly curved helmet surface. Each battery pod 156 further comprises a battery protection circuit 162 for the purpose of protecting the rechargeable batteries from sudden, short-circuit, rapid discharge. As shown in FIG. 5, the container 160 is cut at the top to provide a view to the battery 159 inside.

Each body extension member 106, 108 further comprises an inner surface 116, 118, respectively, each inner surface being comprised partially of an inner surface 166 of battery pods 156 when such are retained within each extension member, each extension member further comprising the outer molded, stylized, aerodynamic surfaces 120, 122. On the inner surfaces 93 and 116 of the body extension member 106, there is a raised area 210 which may be provided with special grippability of silicone material to facilitate retention of the body extension member 106' on a user's helmet. Likewise, on the inner surfaces 95 and 118 of the body extension member 108, there is a raised area 212 which may be provided with special grippability of silicone material to facilitate retention of the body extension member 106 on the user's helmet, hat or head. Surfaces 210 and 212 may be higher in profile (closer to the helmet) than surfaces 116, 118, respectively, or the opposite may be true, where surfaces 210, 212 may be lower in profile than surfaces 116, 118, with surfaces 116, 118 having more grippable material.

Within each body extension member 106, 108 is a battery pod cavity 124, 126, respectively, defined centrally within its corresponding body extension member. The inside of each battery pod cavity 124, 126 comprises a forward surface 128, 130, respectively, a rearward surface 132, 134, respectively, an upper surface 136, 138, respectively, a lower surface 140, 142, respectively, and an outer (still inside) surface 144, 146, respectively. An anterior surface portion of the "pod" looking outer surface 120 opposite cavity 124 is comprised of angled aerodynamic and aesthetically designed surfaces 198, and a posterior surface portion of the retainer 124 is comprised of angled aerodynamic and aesthetically designed surfaces 200. Similarly, an anterior surface portion of the cassette-like retainer 126 is comprised of angled aerodynamic and aesthetically designed surfaces 202, and a posterior portion of the retainer 126 is comprised of angled aerodynamic and aesthetically designed surfaces 204. The pod aspect of the battery pod 156 is introduced and reinforced in that the cassette-like cavity's 124, 126 are reinforced with angular support members 206, 208, respectively, which not only give stability to the preferably silicone, TPU or other rigid structure, solid durometer plastic material, of the cassette or outer pod, but also lends to the aesthetic and aerodynamic functionality and appearance of the cassette.

Figure 3:
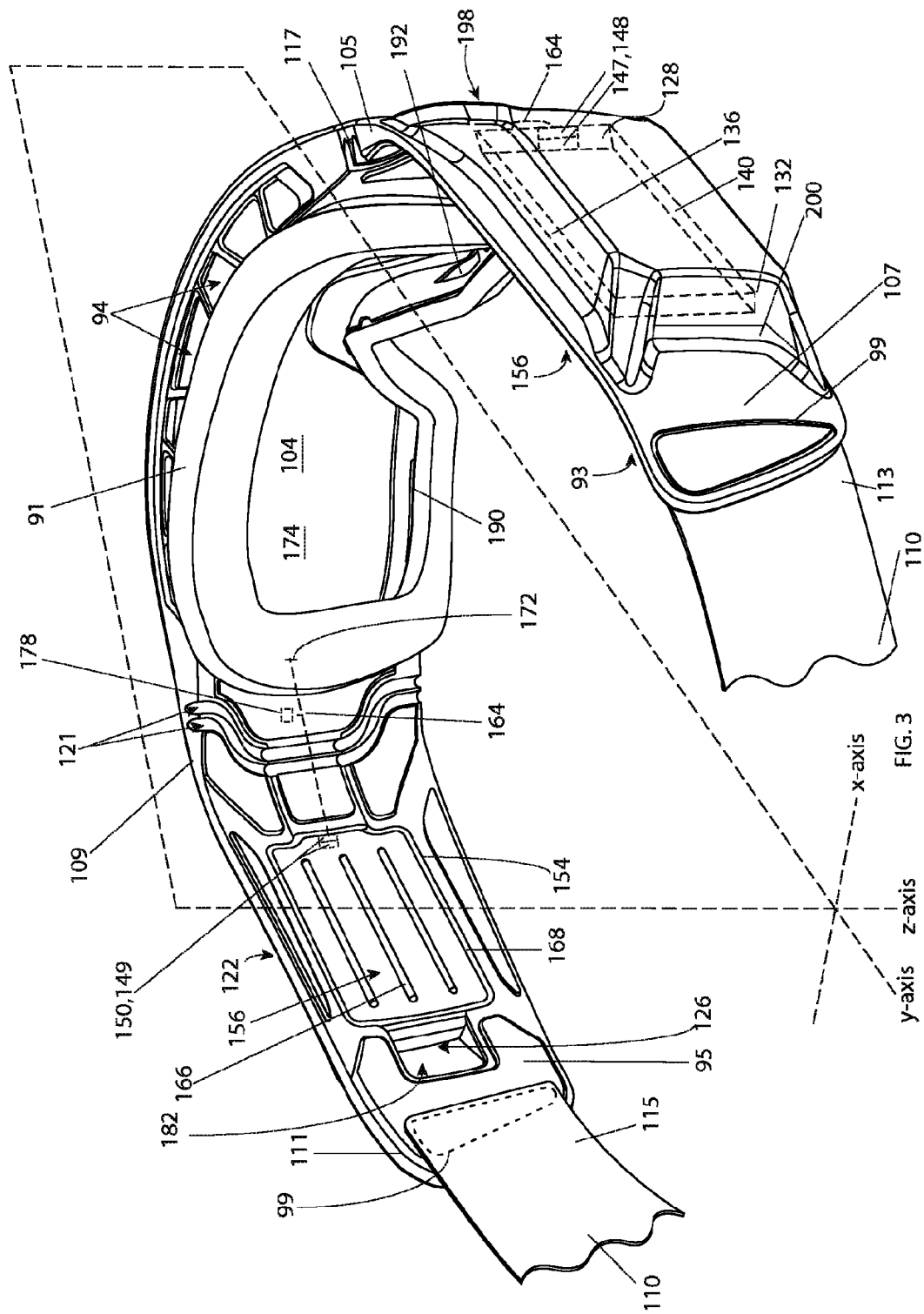
FIG. 3 is a rear left perspective view of a portion of the battery-powered goggle of FIG. 1 and showing superimposed a y-z plane of symmetry.
Figure 10:
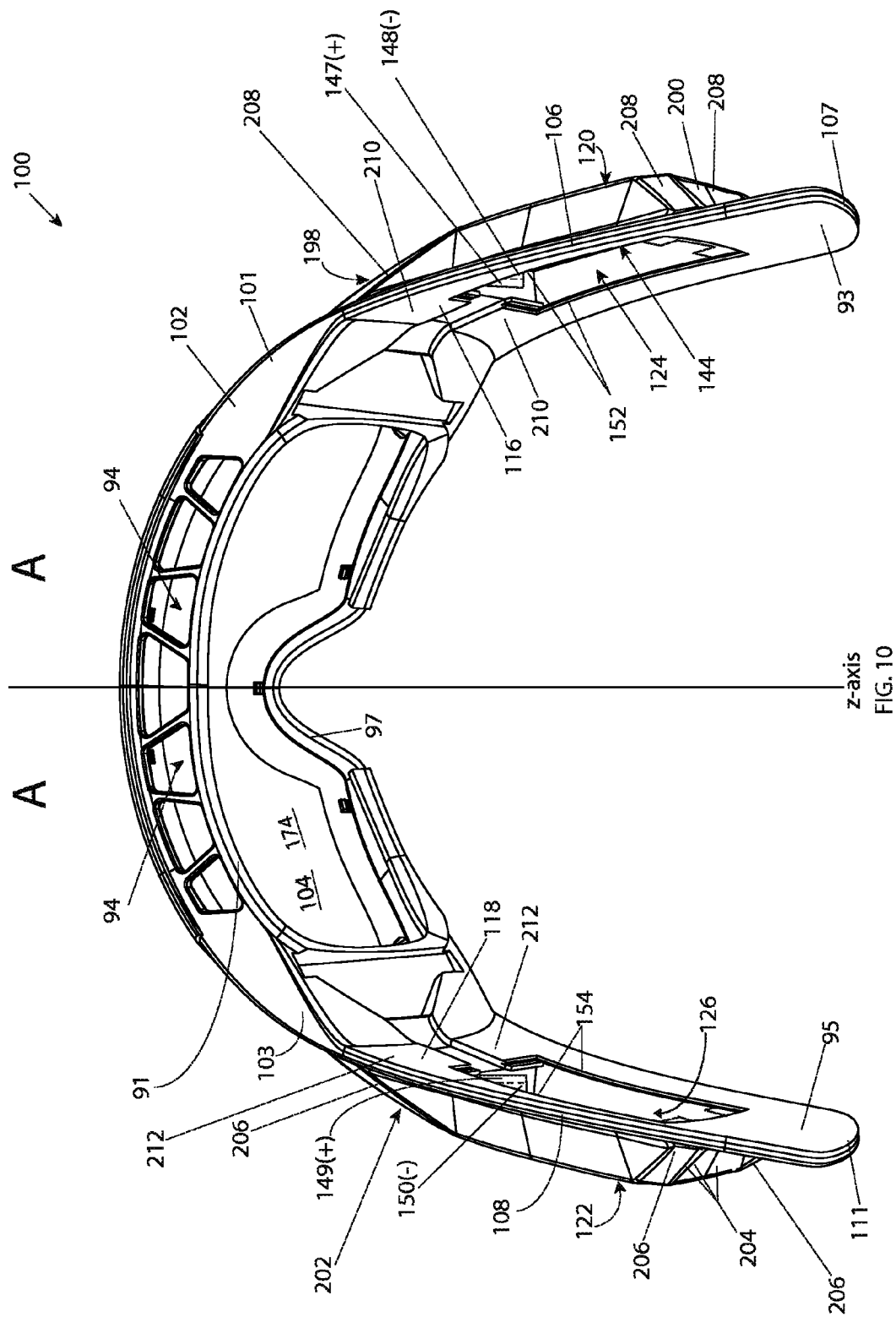
FIG. 10 is a rear perspective view of the goggle of FIG. 1.

Each battery pod cavity 124, 126 is designed to be symmetrical about a y-z plane as shown in FIGS. 3 and 10. On each forward surface 128, 130 there are located positive and negative, preferably spring-biased, contacts 147, 148, 149, 150, respectively. Each cavity 124, 126 is further defined by a lip, or edge, 152, 154, respectively, located around the inner periphery of the opening of each cavity, for retaining a tongue, or retaining member, 168 of each battery pod within the cavity.

At a posterior end of each cavity 124, 126, there is thumb, or other finger, slot 180, 182 for allowing a user to insert his or her finger in the slot to bias the battery pod 156 against the contacts 147, 148, 149, 150, respectively, and to enable clearance of the tongue 158 of each battery pod from being held by a rearward, or posterior, portion of lip 152, 154 of each cavity, respectively.

Each battery pod 156 has positive and negative contacts, 158, 162, respectively, for connecting the battery 159 within the battery pod to circuitry 164 of the goggle outside the battery pod. Preferably the battery pods 156 are comprised of a relatively rigid or solid durometer plastic material, such as TPU or silicone, sealed in water-proof fashion around the battery 159, and therefore the battery is sealed against water intrusion. Further, the design of each cavity 124, 126 is such that water intrusion is minimized, since the preferably silicone or TPU lip 152, 154 of each cavity 124, 126 extends around the periphery of the edge 168 of the battery pod 156, the silicone lip making a seal on the tongue 168, and since the cavity is on the inside surface of each extension member 106, 108, the molded outer surface 120, 122 of each extension member, accommodates the battery pod in a sealed fashion.

Thus, in the goggle 100 of the present invention, the goggle body 102, 103 and the "strap" portions (i.e., body extension members 106, 108) are preferably integrated into, or comprised of, a single unit which extends from the goggle body 102/103 to a position that is adapted to be well over, and even alternatively behind, the ears of a user, as would a conventional strap of a goggle. The purpose of these body extension members 106, 108 is for retaining the batteries 159 in their battery pods 156 of a capacity necessary for powering the goggle for extended periods of time. This preferred embodiment enables not only a better looking and weight-balanced goggle 100, but a more functionally capable goggle in that the heavier batteries 159 able to be supported by such a structure will not sag as otherwise would a conventional strap sag under the increased battery weight or otherwise would be cumbersome to the user. Further, this aspect of the invention enables a preferred inner opening battery cavity 124, 126 structure (i.e., body extension members 106, 108 and the surfaces 128, 132, 134, 138, 144 and surfaces 130, 134, 138, 142, 146, respectively) which is well-sealed in integral silicone that not only grips the user's helmet on its inner surface (including inner surfaces 166 of the battery pod 156, surfaces 93, 95 and surfaces 116, 118 of the extension members 106, 108, respectively) to support the added battery weight, but also seals the system against moisture intrusion.

Each battery 159 may be suitably comprised of a lithium-ion, or lithium-poly, battery conventionally used in cell phones. Preferably the battery 159 is rechargeable within the battery pod 156, the battery pod container 160 preferably being made of plastic resin, or silicone, with the positive and negative external contacts 158, 162, respectively, on the battery pod providing electrical contact through the container external of the battery pod for supplying power to the goggle 100. Goggle 100 further comprises goggle circuit wiring 164, as further shown in FIG. 4, for carrying power from the batteries 159 via the contacts 158, 162 and contacts 147, 148, 149, 150.

Figure 2A:
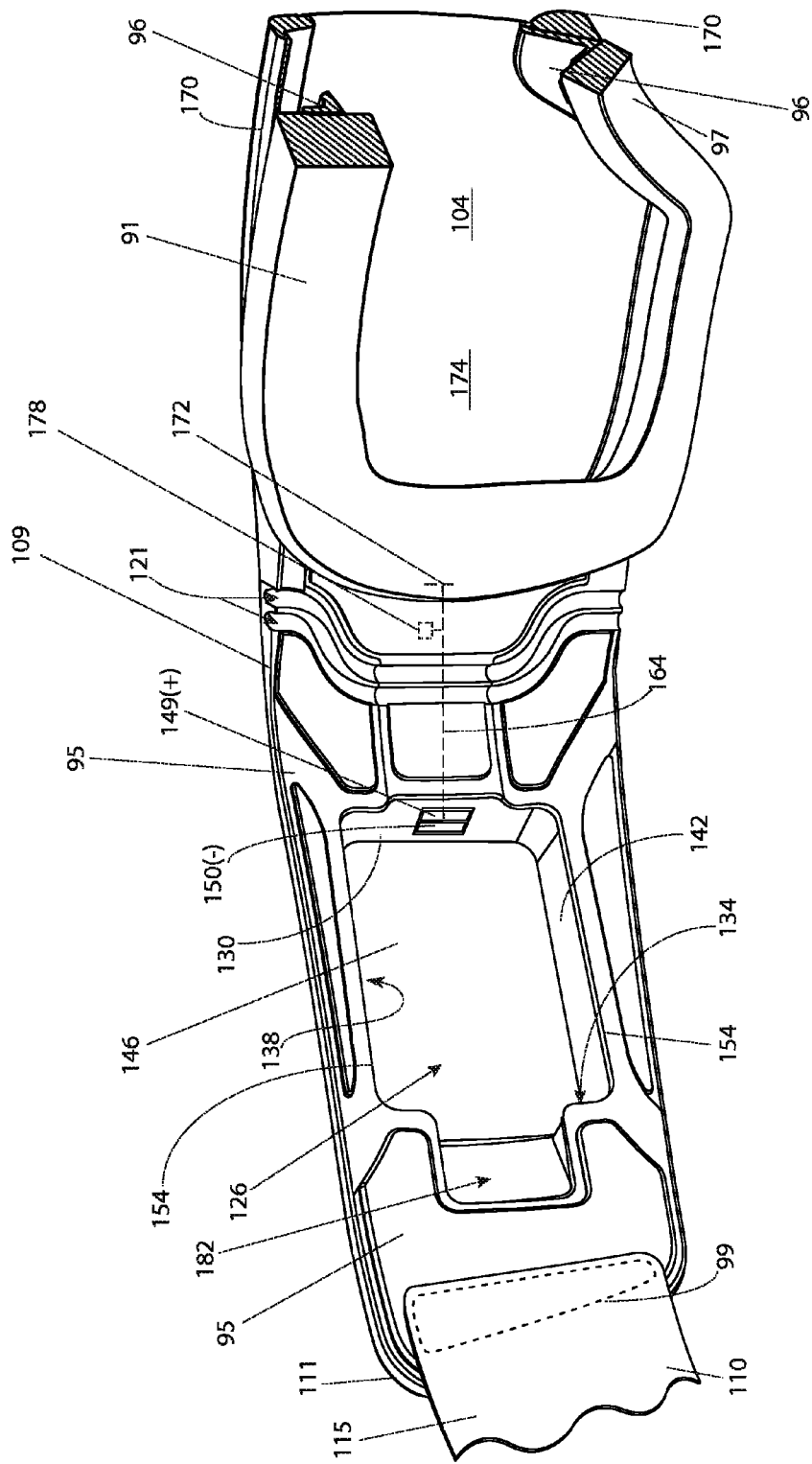
FIG. 2a is a left rear perspective view of a part of the battery-powered goggle of FIG. 1 without a battery pod installed to show the inside of a battery pod cavity.
Figure 2B:
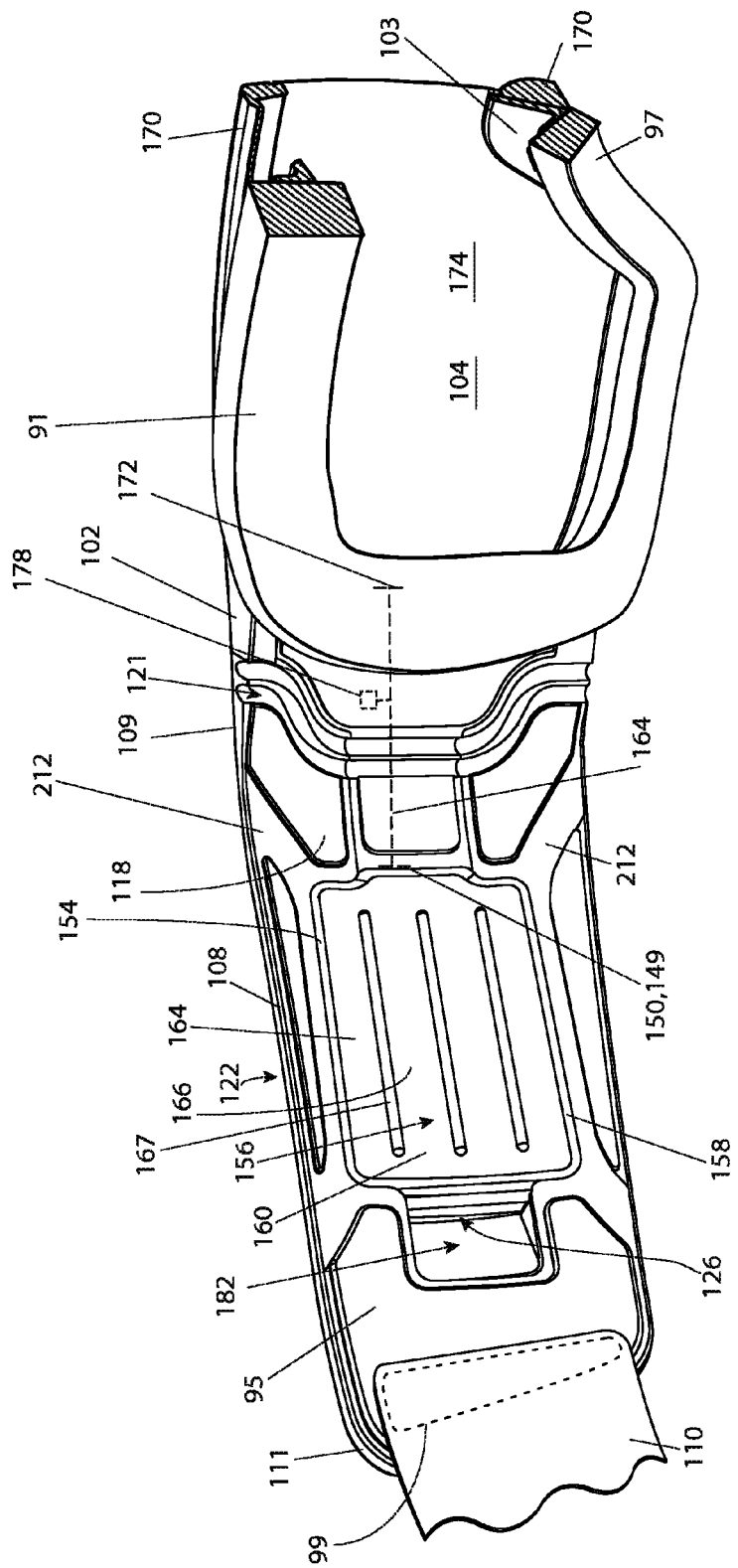
FIG. 2b is a left rear perspective view of a part of the battery-powered goggle of FIG. 1 with a battery pod installed in the battery pod cavity.
Figure 4:
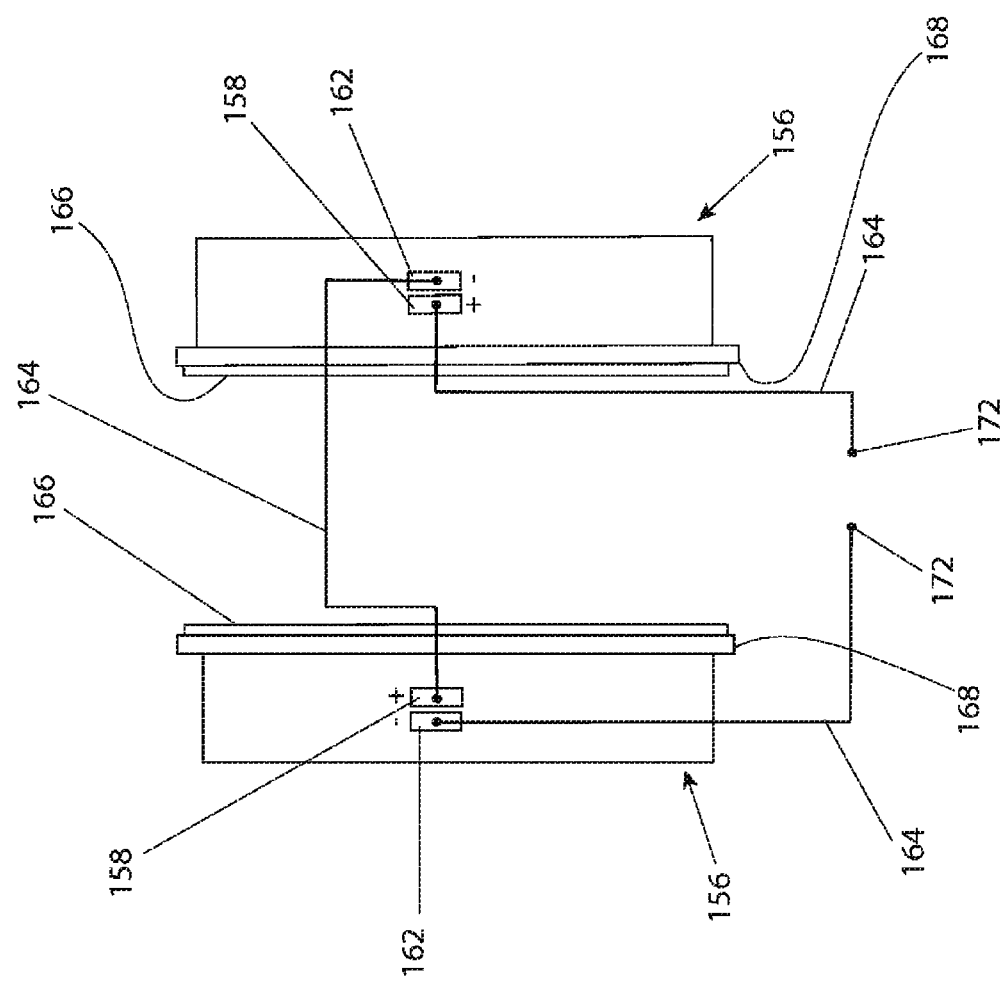
FIG. 4 is a block system and wiring diagram of a battery system in accordance with a portion of the invention shown in FIG. 1.

Circuit wiring 164 preferably comprises a series circuit having contacts as previously described for connection to the battery 159 power source, the circuit further comprising optional contacts for interconnecting the circuit wiring 164, and hence the batteries 159, with the resistive heating element 174 via contacts 172 between the resistive heating element and the circuit. Since the goggle is to be substantially symmetrical on either side of the y-z plane shown in FIG. 3, this means that the cavity contacts 147, 148, 149, 150 are configured so that the same polarity contact is on the inside (relative to the y-z plane) in each battery pod cavity 124, 126 and the same polarity contact is on the outside (relative to the y-z plane) in each battery pod cavity. It doesn't matter which polarity contact is on the inside and which polarity contact is on the outside, just that they are consistently oriented to the battery pod 154 configuration. Thus, for example, as shown in FIGS. 2a and 4, the outer contact 150 is designated as the negative contact, and the inner contact 149 is designated as the positive contact. Further, accordingly, as shown in FIGS. 3 and 4, the outer contact 148 is designated as the negative contact, and the inner contact 147 is designated as the positive contact. This fact enables use of the same battery pod 156 in either cavity 124, 126, as illustrated specifically in FIG. 8, by simply flipping, or rotating, the battery pod about the z axis and installing it in the other cavity. In this way, a single type of battery pod 156 is able to be used in either cavity, thus reinforcing the symmetry in appearance of the overall power system. To enable this symmetry in appearance, the circuit wiring 164 in the goggle 100 is preferably wired in series as shown in FIG. 4 with opposite poles of each battery being interconnected and with the contacts to the other electronics, such as the heating element 174 of lens 104, being interposed between one of these opposite pole interconnections. A more complete electrical diagram for wiring of electronics in the goggle may be found in U.S. Pat. No. 8,566,962 B2 to Cornelius, for PWM Heating System for Eye Shield, incorporated herein by reference, which teaches a system for more efficient use of battery power in lens heating operations, thus addressing the fact that lens heating operations have consumed substantial battery power beyond that conveniently wearable on the strap of a goggle.

The goggle 100 also preferably comprises a charging port 176 and charging circuit that may be interconnected with circuit wiring 164. Accordingly, the batteries 159 may be charged via the charging port 176 on an under surface of the goggle 100. The charging port 176 may be plugged with a suitable plug (not shown) when not in use, to prevent the intrusion of moisture into the electronic system. Further depending from circuit wiring 164 is a processor 178 for the purpose of controlling electronic functions of the goggle, such as video capture, GPS functionality, indicator lights, heads-up display and/or heating, etc.

Electrical circuitry 164 may advantageously be like that shown in that application with contacts (e.g., buss bars) on the lens being similar to those shown and described and with the circuitry 164 running through the goggle body 102/103 to interconnect the resistive-film heating means 174, the battery 159, the USB, or other power connection, charging receptacle 176, the on/off button 188 and any other power level adjustments or other electronic controls as will be apparent to those of skill in the art of electronics.

The goggle body 102/103 and extension members may be made of a plastic resin, silicone rubber or other material suitably flexible for conforming to the contours of a user's head, while also having sufficient rigidity to appropriately retain in substantially fixed position the weight of the battery pods 156 and the lens 104. The goggle lens 104 may be made of an optical quality polycarbonate plastic material. The battery pods 156 may be made of silicone rubber or other sufficiently rigid material to ensure good frictional or other retention of the battery pod in the battery pod cavity 124, 126, to ensure good wear characteristics and to ensure good gripping of a user's helmet. Because of the inherent weight of the battery pods 156 and the extension members 106, 108, the grippability of the silicone on a user's helmet is an important factor in retaining the goggle on the helmet without sagging or sliding down during exertion of activity and encounter of bumps and jolts commonly encountered in snowboarding or skiing.

The textile strap portion 110 may comprise a conventional adjustable elastomeric strap that is stretchy, and yet resilient, so as to allow comfortable retention of the goggle 100 on the user's head or a helmet. The length of the strap 110 is adjustable via adjustment members 184, 186.

The goggle 100 also preferably comprises at least an on-off switch 188 (in reality this is typically an on and very low power switch) for allowing power to the goggle lens 104 and/or other goggle electronics. Further, other heating power controls, such as a power level control switch, and a battery level indicator switch, as described more in detail in U.S. patent application Ser. No. 13/587,908 to McCulloch et al., may be incorporated into the electronics and power system of the present invention without departing from the true scope and spirit of the invention as set forth in the appended claims. Yet further, switching and control systems 178 may be provided for as part of the present goggle 100 for enhanced functionality of a GPS system, a video capturing system, a sound system, or other electronic device, as such switching is described in the prior art. Such switching and control systems 178 may be run off of the circuit wiring 164 and battery power and control of the present goggle 100 without departing from the true scope and spirit of the invention.

Upon depressing the on/off button, or switch, 188, power from the batteries 159 is connected to the resistive heating film, or element, on the lens 104. Likewise, any other electronics of the goggle 100 may be switched on with the main power switch 188, whereas other controls may be implemented, for example to set the power level of the heating element of the lens to zero level as may be desired and as further described in U.S. Pat. No. 8,566,962 B2, for PWM Heating System for an Eyeshield, to Cornelius. Alternatively, a battery-strength indicator 190, and a heat, or power level, indicator 192, may be displayed preferably within the goggle 100 to the user of the goggle. Depressing the on/off button 100 again may be implemented to turn off the heat, or more accurately reduce it to an extremely low power state. After a short time, preferably, the indicators 190, 192 turn off so as to not unduly distract the user. The circuitry 164 also interconnects a standard USB or other power connector charging receptacle 176, the battery 159, logic for controlling power on/off, power level increase/decrease, power level indication, and battery level indication using electric light pipes, for example.

Figure 6:
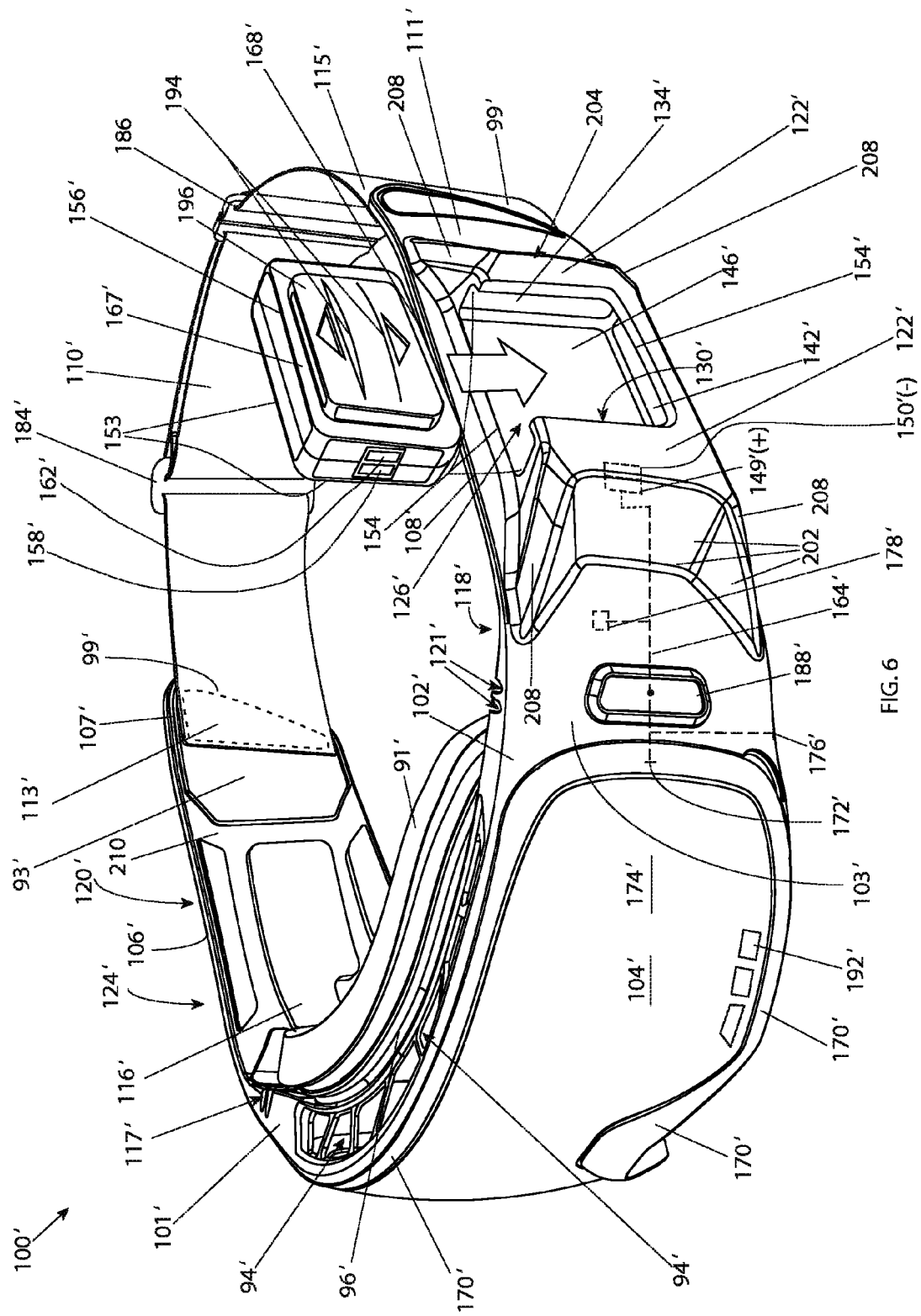
FIG. 6 is a right front perspective view of an alternate embodiment of the invention showing the battery pods accessible from an outer portion of the strap.
Figure 7:
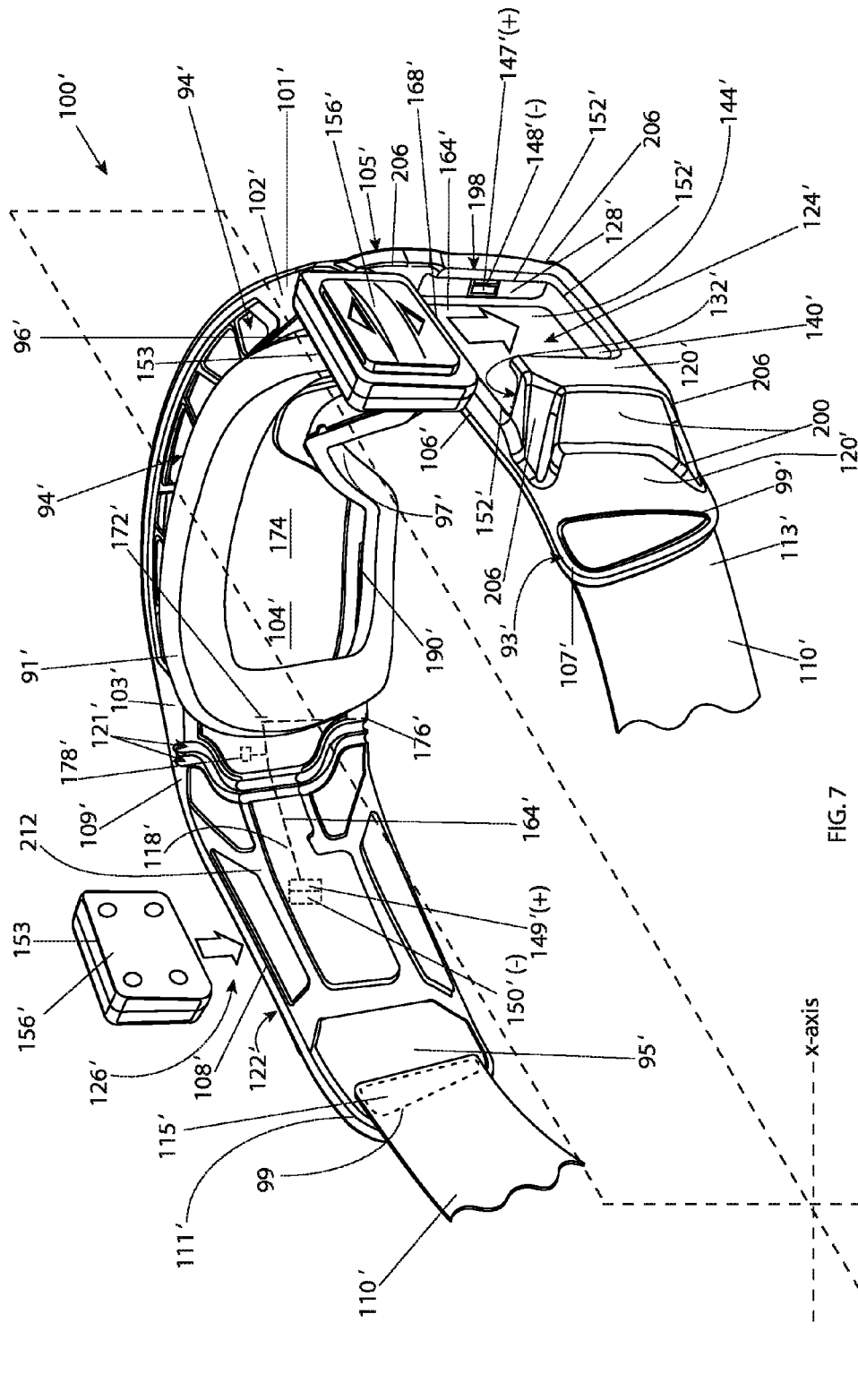
FIG. 7 is a left rear perspective view of a portion of the alternate embodiment of the goggle of FIG. 6.
Figure 8:
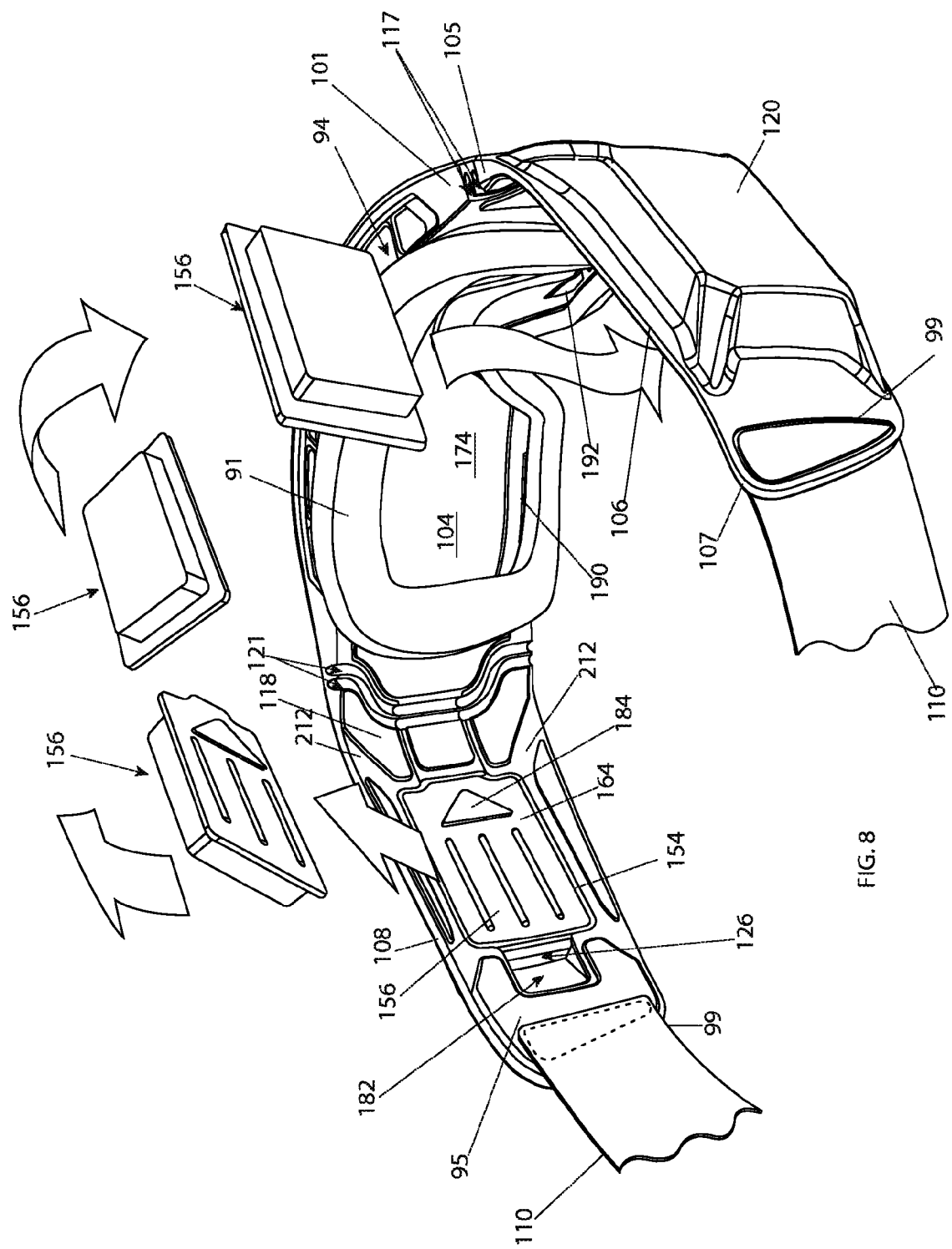
FIG. 8 is a left rear perspective view of a portion of the goggle of FIG. 1 further illustrating how the same battery pod is able to be used in either battery pod cavity by rotating the battery pod about a central (z) axis of the goggle.
Figure 9:
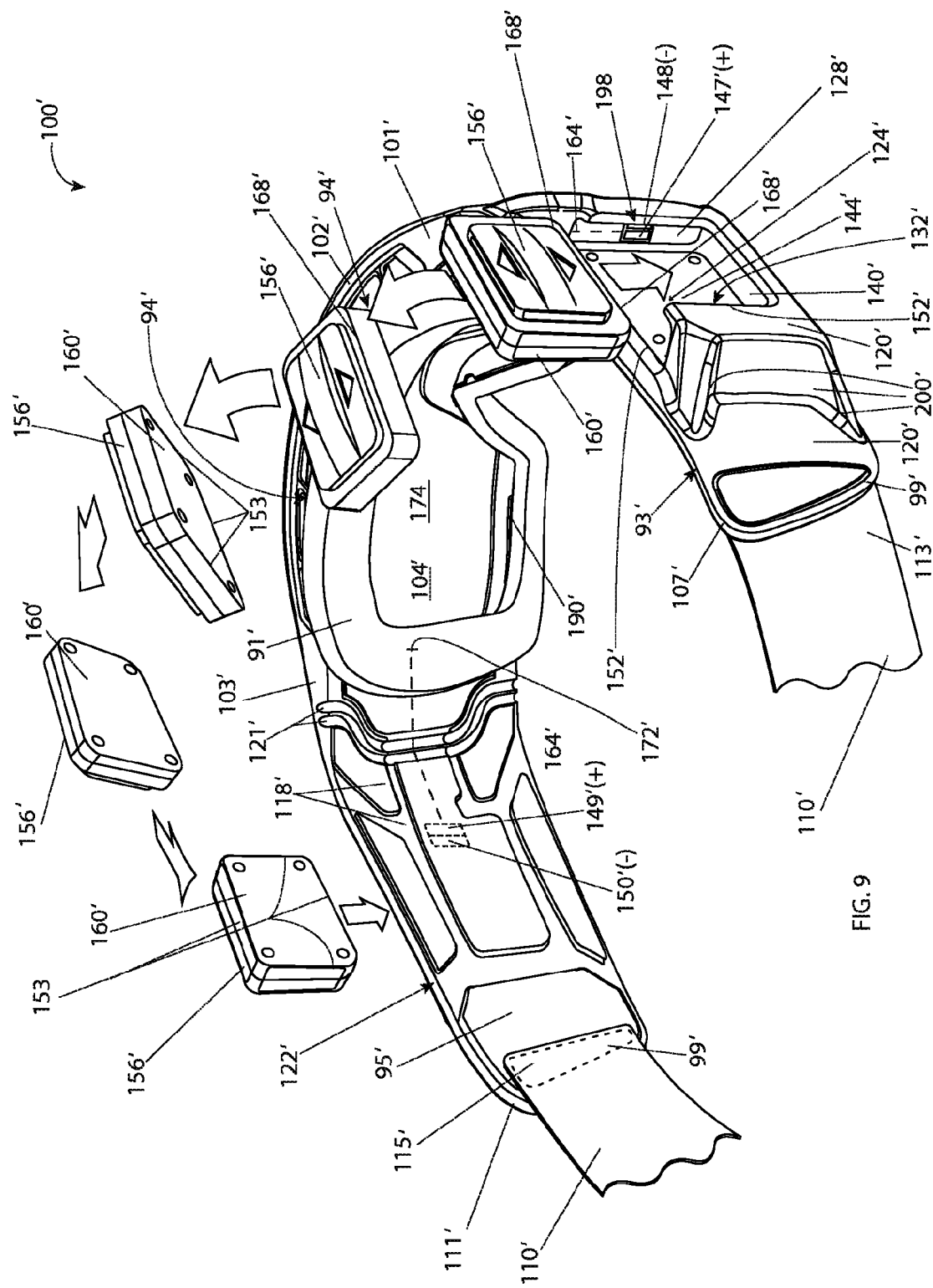
FIG. 9 is a left rear perspective view of a portion of the alternate embodiment of the goggle of FIG. 6 further illustrating how the same battery pod is able to be used in either battery pod cavity by rotating the battery pod about a central (z) axis of the goggle.

Referring now to FIGS. 6, 7 and 9, an alternate embodiment goggle 100' is shown. Goggle 100' comprises a multi-pod, symmetrically-balanced, goggle-strap-mounted power supply system. The goggle 100' comprises a body 102' having ends 101', 103', a lens 104' installed in the body, a plurality of body extension members 106', 108' and an elastic, stretchy, textile strap portion 110' having ends 113', 115'. The goggle 100' also preferably comprises a flexible, spongy, foam interface peripheral member 91' attached around a posterior periphery 96' of the goggle body 102'. The foam interface member 91' is for interfacing with the user's face and the posterior portion 96' of the anterior portion 102' of the goggle body, and is for interfacing with the lens 104'. The posterior flexible and spongy portion 91' of the body 102' engages the user's face around the user's eyes and on the bridge of the user's nose at 97', while the anterior periphery body member 102' provides a base or foundation upon which the lens 104' is engaged. Further, the goggle body 102' may be provided with conventional ventilation ports 94' in the anterior portion of the goggle body.

As mentioned in connection with the primary embodiment of the invention, incorporation by reference is made herein of U.S. patent application Ser. No. 13/587,908, for Goggle with Easily Interchangeable Lens that is Adaptable for Heating to Prevent Fogging, to McCulloch et al., wherein an interchangeable series of lenses are shown and described having varying types of resistive element, or resistive film, heating elements thereon, or alternatively having no heating element on the lens at all without departing from the scope and spirit of the invention, the goggle of this alternate embodiment of the invention set forth in the present application likewise employing similar lens types. In the case where there is no lens heating operation involved, the battery pods 156' would be useful to power other electronic functions of the goggle 100', such as GPS, video, audio sound, heads-up display, and other electronic functions. Similarly to that described in the co-pending Ser. No. 13/587,908 application to McCulloch et al., the lens 104' of the present invention is preferably easily interchangeable as shown and described in that patent application. The lens 104' may be a clear lens, or a tinted lens as known in the art, and preferably has a clear anti-fog resistive coating 174' on an inner surface of the lens, the coating further being protected with a protective layer, or double-lens construction, to protect the anti-fog surface from being scratched off. The anti-fog resistive coating 174' preferably comprises an Indium Tin Oxide (ITO) compound that may be sprayed, deposited with a known ion-sputtering technique, painted or otherwise layered or applied. The film heating member 174' may be comprised of another material designed in the form of a resistive element that generates heat when connected to an electrical circuit without departing from the true scope and spirit of the invention.

The goggle 100' further comprises a lens frame, or bezel 170', upon which the lens 104' is retained, as for example with adhesive, and the bezel further comprises engagement, e.g., a tongue and groove engagement means, or cap and ridge engagement means as described in the aforementioned patent application to McCulloch et al. Still further, the lens 104'/bezel 170' comprises interconnection means, for example snaps, hooks, silicone nubs or latches, both operative to engage and secure connection with a lens contact portion 172', if any, of the goggle 100', for interconnecting a heating element portion 174' on the inner surface of the lens 104' with the batteries.

Since the lens 104' is easily interchangeable, a user may have multiple such lens 104'/bezel 170' combinations, each such lens comprising alternate tinted lens surfaces of varying colors and/or degree of tint, again either with or without anti-fog resistive coating thereon. This feature provides that either anti-fog or non-anti-fog lenses may be used with the goggle 100' of the invention without damaging the system or even reducing battery life. This is because the electrical system of the goggle 100' is preferably a low-power system which enables safe usage of the goggle with a heated lens 104', or with a non-heated lens 104', in the goggle. This feature makes use of the goggle more care-free and flexible, as whether the battery is in use, or not, the user is encouraged in choosing a goggle 100' that suits the weather, terrain, and lighting conditions of the moment.

The body extension member 106' comprises first and second ends, 105', 107' and inner and outer surfaces 93' and 120', respectively. The body extension member 108 comprises first and second ends 109', 111' and inner and outer surfaces 95' and 122', respectively. The body extension members 106', 108' comprise in part what would otherwise be side portions of a strap of a conventional goggle. In other words, the body extension members 106', 108' are in the same location relative to a user's head as would the side portions of a strap of a conventional goggle. The first end 105', 109' of each body extension member 106', 108' extends from a corresponding end 101', 103', respectively, of the goggle body 102'. As shown, accordion-type, serpentine, reticulation channel means 117', 121' may be employed between the goggle body 102' and each body extension member 106', 108', respectively, in order to ensure sufficient flexibility to the strap-type function of each body extension member to enable easy adaptation of the goggle to differently-shaped users and their various head and helmet shapes and sizes. The second end 107', 111' of each body extension member 106', 108' is attached to corresponding ends 113', 115', respectively, of the textile strap portion 110' of the strap (comprised of each extension member 106', 108' and the textile portion 110'). Such attachment may be accomplished by looping the ends 113', 115' of the strap 110' around pins (not shown) embedded into the second ends 107', 111' of the body extension members 106', 108', or other means of interconnecting such dissimilar elements known in the art, such as by stitching 99'.

The goggle 100' further comprises a plurality of battery pods 156'. Each battery pod 156' comprises a container 160' that is sealed around the battery inside. Each battery pod 156' further comprises a battery protection circuit (not shown) for the purpose of protecting the rechargeable batteries from sudden, short-circuit, rapid discharge.

Each body extension member 106', 108' further comprises an inner surface 116', 118', respectively, each extension member further comprising the outer molded, stylized, aerodynamic surfaces 120', 122'. Within, and defined so as to be accessible from the exterior of each body extension member 106', 108' is a battery pod cavity 124', 126', respectively, defined centrally within its corresponding body extension member. The inside of each battery pod cavity 124', 126' comprises a forward surface 128', 130', respectively, a rearward surface 132', 134', respectively, a lower surface 140', 142', respectively, and an inner surface 144', 146', respectively. Each battery pod cavity 124', 126' is designed to be symmetrical about a y-z plane as shown in FIG. 7. On each forward surface 128', 130' there are located positive and negative, preferably spring-biased, contacts 147', 148', 149', 150', respectively. Each cavity 124', 126' is further defined by a plurality of lips, or edges, 152', 154', respectively, located around the inner periphery of the opening of each cavity, for retaining back edges 153 of the battery pod 156' to retain the battery pod within the cavity. In effect, surfaces 120', 128', 132', 140', 144', and lips 152' define a cassette-like retainer, otherwise known as cavity 124', in which the battery pod 156' is retained. An anterior surface portion of the cassette-like retainer 124' is comprised of angled aerodynamic and aesthetically designed surfaces 198', and a posterior surface portion of the retainer 124' is comprised of angled aerodynamic and aesthetically designed surfaces 200'. Similarly, on the other side of the goggle 100', surfaces 122', 130', 134', 142', 146' and lips, or edges, 154' define another cassette-like retainer, otherwise known as cavity 126', in which the battery pod 156' is retained. An anterior surface portion of the cassette-like retainer 126' is comprised of angled aerodynamic and aesthetically designed surfaces 202', and a posterior portion of the retainer 126' is comprised of angled aerodynamic and aesthetically designed surfaces 204'. The pod aspect of the battery pod 156' is introduced and reinforced in that the cassette-like cavity's 124', 126' are reinforced with angular support members 206', 208', respectively, which not only give stability to the preferably TPU or silicone structure of the cassette, but also lends to the aesthetic and aerodynamic functionality and appearance of the cassette.

On the inner surfaces 93' and 116' of the body extension member 106', there is a raised area 210' which may be provided with special grippability of silicone material to facilitate retention of the body extension member 106' on a user's helmet. Likewise, on the inner surfaces 95' and 118' of the body extension member 108', there is a raised area 212' which may be provided with special grippability of silicone material to facilitate retention of the body extension member 106' on the user's helmet. Surfaces 210' and 212' may be higher in profile (closer to the helmet) than surfaces 116', 118', respectively, or the opposite may be true, where surfaces 210', 212' may be lower in profile than surfaces 116', 118', with surfaces 116', 118' having more grippable material.

On an exterior surface of each battery pod 156', there are upper and lower thumb, or finger, catches 194 for allowing a user to grip the battery pod to press the battery pod into a cavity 124', 126', or alternatively to remove the battery pod from a cavity. Adjacent each of these catches 194 are up and down arrow indicia 196, indicating the direction in which the battery pod 156' may be inserted into, and removed from, a cavity 124', 126'. Thus, a user is enabled in using his or her finger on the catch 194 to bias the battery pod 156' into a respective cavity 124', 126' and against the contacts 147', 148', or 149', 150'. Each battery pod 156' also comprises a raised area 196 on an outside surface 167' of the battery pod. Insertion of the battery pod 156' into a cavity 124', 126' by a user proceeds until an edge portion of the outside surface 167' hits lower lip 152', 154', respectively. The battery pod 156' is held in place and sealed against moisture intrusion by a rearward, or posterior, portion of lip 152', 154' of each cavity, respectively.

Each battery pod 156' has positive and negative contacts, 158', 162', respectively, for connecting the battery within the battery pod to circuitry 164' of the goggle outside the battery pod. Preferably the battery pods 156' are comprised of plastic resin or silicone sealed in water-proof fashion around the battery, and therefore the battery is sealed against water intrusion. Further, the design of each cavity 124', 126' is such that water intrusion is minimized into the cavity, since the preferably silicone or TPU lip 154' of each cavity 124', 126' extends around the periphery of the edge 168' of the battery pod 156, the silicone lip making a seal on the edge 168' to prevent excess water from getting into the cavities. Water intrusion may also be further prevented within the cavities 124', 126' with a liftable flap (essentially an extension of lips 152', 154').

Thus, in the goggle 100' of the present invention, the goggle body 102', 103' and the "strap" portions (i.e., body extension members 106', 108') are preferably integrated into, or comprised of, a single unit which extends from the goggle body 102'/103' to a position that is adapted to be well over, and even alternatively behind, the ears of a user, as would a conventional strap of a goggle. The purpose of these body extension members 106', 108' is for retaining the battery pods 156' of a capacity necessary for powering the goggle for extended periods of time. This enables not only a better looking and weight-balanced goggle 100', but a more functionally capable goggle in that the heavier batteries able to be supported by such a structure will not sag as otherwise would a conventional strap sag under the increased battery weight or otherwise would be cumbersome to the user. Further, this aspect of the invention enables a cassette-like opening battery cavity 124', 126' structure (i.e., body extension members 106', 108' and the surfaces 128', 132', 134', 138', 144' and surfaces 130', 134', 138', 142', 146', respectively) which is well-sealed in integral silicone that not only grips the user's helmet on its inner surface (including surfaces 93', 95' and surfaces 116', 118', respectively, of the extension members 106', 108') to support the added battery weight, but also seals the system against moisture intrusion.

Each battery pod 156' may be suitably comprised of a lithium-ion, or lithium-poly, battery conventionally used in cell phones. Preferably the battery is rechargeable within the battery pod 156', the battery pod container 160' preferably being made of plastic resin, or silicone, with the positive and negative external contacts 158', 162', respectively, on the battery pod providing electrical contact through the container external of the battery pod for supplying power to the goggle 100'. Goggle 100' further comprises goggle circuit wiring 164', as further shown in FIGS. 6, 7 and 9, for carrying power from the battery pods 156' via the contacts 158', 162' and contacts 147', 148', 149', 150'.

Figure 11:
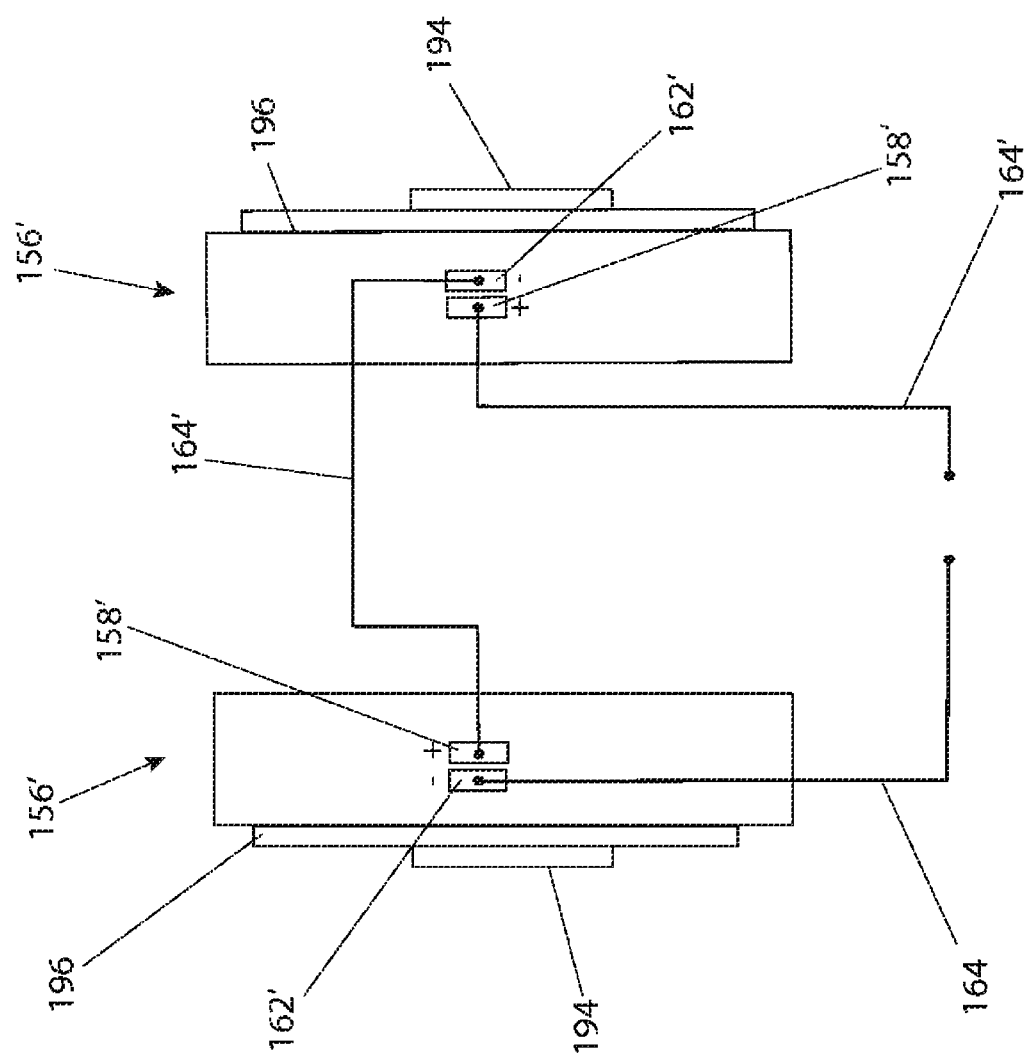
FIG. 11 is a block system and wiring diagram of a battery system in accordance with a portion of the alternate embodiment of the invention of FIG. 6.

Circuit wiring 164' preferably comprises a series circuit having contacts as previously described for connection to the battery pod 156 power sources, the circuit further comprising optional contacts for interconnecting the circuit wiring 164', and hence the battery pods 156', with the resistive heating element 174' via contacts 172' between the resistive heating element and the circuit. Since the goggle is to be substantially symmetrical on either side of the y-z plane shown in FIG. 7, this means that the cavity contacts 147', 148', 149', 150' are configured so that the same polarity contact is on the inside (relative to the y-z plane) in each battery pod cavity 124', 126' and the same polarity contact is on the outside (relative to the y-z plane) in each battery pod cavity. It doesn't matter which polarity contact is on the inside and which polarity contact is on the outside, just that they are consistently oriented to the battery pod 154' configuration. Thus, for example, as shown in FIGS. 7 and 11, the outer contact 150' is designated as the negative contact, and the inner contact 149' is designated as the positive contact. Further, accordingly, the outer contact 148' is designated as the negative contact, and the inner contact 147' is designated as the positive contact. This fact enables use of the same battery pod 156' in either cavity 124', 126', as illustrated specifically in FIG. 9, by simply flipping, or rotating, the battery pod about the z axis and installing it in the other cavity. In this way, a single type of battery pod 156' is able to be used in either cavity, thus reinforcing the symmetry in appearance of the overall power system. To enable this symmetry in appearance, the circuit wiring 164' in the goggle 100' is preferably wired in series as shown in FIG. 11 with opposite poles of each battery being interconnected and with the contacts to the other electronics, such as the heating element 174' of lens 104', being interposed between one of these opposite pole interconnections.

A more complete electrical diagram for wiring of electronics in the goggle may be found in U.S. Pat. No. 8,566,962 B2, to Cornelius, for PWM Heating System for Eye Shield, incorporated here by reference, which teaches a system for more efficient use of battery power in lens heating operations, thus addressing the fact that lens heating operations have consumed substantial battery power beyond that conveniently wearable on the strap of a goggle.

The goggle 100' also preferably comprises a charging port 176' and charging circuit that may be interconnected with circuit wiring 164'. Accordingly, the battery pods 156' may be charged via the charging port 176', shown on an under surface of the goggle 100'. It will be appreciated that the charging port of the goggle may be located on any convenient surface of the goggle body with due consideration being given to sealing the port. Or alternatively, the goggle battery may be charged by placing it on a charging mat as is known in the art. The charging port 176' may be plugged with a suitable plug (not shown) when not in use, to prevent the intrusion of moisture into the electronic system. Further depending from circuit wiring 164' is a processor 178' for the purpose of controlling electronic functions of the goggle, such as video capture, GPS functionality, indicator lights, heads-up display and/or heating, etc.

The electrical circuitry 164' may advantageously be like that shown in that application to Cornelius with contacts (e.g., buss bars) on the lens being similar to those shown and described and with the circuitry 164' running through the goggle body 102'/103' to interconnect the resistive-film heating means 174', the battery pod 156', the USB, or other power connection, charging receptacle 176', the on/off button 188' and any other power level adjustments or other electronic controls as will be apparent to those of skill in the art of electronics.

The goggle body 102'/103' and extension members may be made of a plastic resin, silicone rubber or other material such thermal plastic urethane, sometimes called TPU, that is suitably flexible for conforming to the contours of a user's head, while also having sufficient rigidity to appropriately retain in substantially fixed position the weight of the battery pods 156' and the lens 104'. The goggle lens 104' may be made of an optical quality polycarbonate plastic material. The battery pods 156' may be made of plastic resin, silicone rubber or other sufficiently rigid material to ensure good frictional or other retention of the battery pod in the battery pod cavity 124', 126'. Because of the inherent weight of the battery pods 156' and the extension members 106', 108', the grippability of the silicone on a user's helmet is an important factor in retaining the goggle on the helmet without sagging or sliding down during exertion of activity and encounter of bumps and jolts commonly encountered in snowboarding or skiing.

The textile strap portion 110' may comprise a conventional adjustable elastomeric strap that is stretchy, and yet resilient, so as to allow comfortable retention of the goggle 100' on the user's head or a helmet. The length of the strap 110' is adjustable via adjustment members 184', 186'.

The goggle 100' also preferably comprises at least an on-off switch 188' (in reality this is typically an on and very low power switch) for allowing power to the goggle lens 104' and/or other goggle electronics. Further, other heating power controls, such as a power level control switch, and a battery level indicator switch, as described more in detail in U.S. patent application Ser. No. 13/587,908 to McCulloch et al., may be incorporated into the electronics and power system of the present invention without departing from the true scope and spirit of the invention as set forth in the appended claims. Yet further, switching and control systems 178' may be provided for as part of the present goggle 100' for enhanced functionality of a GPS system, a video capturing system, a sound system, or other electronic device, as such switching is described in the prior art. Such switching and control systems 178' may be run off of the circuit wiring 164' and battery power and control of the present goggle 100' without departing from the true scope and spirit of the invention.

Upon depressing the on/off button, or switch, 188', power from the battery pods 156' is connected to the resistive heating film, or element, on the lens 104'. Likewise, any other electronics of the goggle 100' may be switched on with the main power switch 188', whereas other controls may be implemented, for example to set the power level of the heating element of the lens to zero level as may be desired and as further described in U.S. Pat. No. 8,566,962 B2, for PWM Heating System for an Eyeshield, to Cornelius. Alternatively, a battery-strength indicator 190', and a heat, or power level, indicator 192', may be displayed preferably within the goggle 100' to the user of the goggle. Depressing the on/off button 188' again may be implemented to turn off the heat, or more accurately reduce it to an extremely low power state. After a short time, preferably, the indicators 190', 192' turn off so as to not unduly distract the user. The circuitry 164' also interconnects a standard USB or other power connector charging receptacle 176', the battery pod 156', logic for controlling power on/off, power level increase/decrease, power level indication, and battery level indication using electric light pipes, for example.

While a preferred embodiment of the present invention has been shown and described, it will be apparent to those skilled in the art that modifications may be made without departing from broader aspects of the invention. The appended claims are therefore intended to cover all such changes and modifications as fall within the true spirit and scope of the invention.

What is claimed is:

1. A battery-powered goggle capable of performing a powered function within the goggle comprising:
 a goggle body having wiring therein and first and second ends;
 a lens retained within said goggle body;
 first and second extension members connected to said goggle body, each said extension member having a first end, a second end, an inner surface and an outer surface, each said extension member having wiring therein connected to the wiring in said goggle body for interconnecting a battery to the wiring in said goggle body, each said extension member defining at least one concave molded cavity open to one of the inner surface of the extension member and the outer surface of the extension member and having defined within the cavity contacts for interconnecting the battery to the wiring in said extension member, the first end of each said extension member being connected with respective first and second ends of the goggle body;
 a strap portion having first and second ends, the first end of said strap portion being connected with the second end of said first extension member and the second end of said strap portion being connected with the second end of said second extension member;
a plurality of batteries;
a plurality of battery pods, each said battery pod comprising a container containing at least one of said batteries and adapted for being releasably retained in any cavity of any said extension member, each said battery pod adapted for providing a contact between at least one of said batteries in the container and the contacts within any cavity of any said extension member, whereby transmission of power from the batteries to power the goggle is enabled.

2. The goggle of claim 1, wherein each said extension member is semi-flexible in lateral and transverse directions, each extension member also being resistant to stretching in a longitudinal direction.

3. The goggle of claim 2, wherein each said extension member and said goggle body are made of contiguous silicone.

4. The goggle of claim 1, wherein each said extension member further defines a channel for the wiring.

5. The goggle of claim 1, wherein each battery, battery pod and cavity contact further comprises a pair of contacts comprising a positive and a negative polarity contact, and wherein each cavity and pair of cavity contacts are located in a corresponding said extension member, each cavity and pair of cavity contacts being located symmetrically about a transverse plane through said goggle body and oriented so that each cavity opens to the inside surface of each said extension member and each positive cavity contact and each negative cavity contact is oriented symmetrically about the transverse plane, wherein each said battery pod is the same and capable of being releasably retained in any one of the cavities in said extension members.

6. A dual-battery-pod powered goggle capable of heating the lens of the goggle, comprising:
a goggle body having wiring therein and first and second ends;
a lens retained within said goggle body, said lens having a resistive heating element thereon interconnected with the wiring in said goggle body;
first and second extension members integrally connected to said goggle body, each said extension member having a first end, a second end, an inner surface and an outer surface, each said extension member having wiring therein connected to the wiring in said goggle body for interconnecting a battery to the wiring in said goggle body, each said extension member defining a concave molded cavity open to the inner surface of the extension member and having defined within the cavity contacts to enable interconnecting of the battery to the wiring in said extension member, the first end of each extension member being integrally connected with respective first and second ends of the goggle body;
a strap portion having first and second ends, the first end of said strap portion being connected with the second end of said first extension member and the second end of said strap portion being connected with the second end of said second extension member;
a plurality of batteries;
two battery pods, each said battery pod comprising a container containing at least one of said batteries and adapted for being releasably retained in any cavity of said extension members, each said battery pod adapted for providing a contact between at least one of said batteries in the container and the contacts within any cavity of any said extension member, whereby transmission of power from the batteries to heat the goggle lens is enabled.

7. The goggle of claim 6, wherein each said extension member and said strap member are comprised of integral silicone rubber.

8. The goggle of claim 7 wherein each said extension member further defines a channel for the wiring.

9. The goggle of claim 6, wherein each battery, battery pod and cavity contact further comprises a pair of contacts comprising a positive and a negative polarity contact, and wherein each cavity and pair of cavity contacts are located in a corresponding said extension member, each cavity and pair of cavity contacts being located symmetrically about a transverse plane through said goggle body and oriented so that each positive cavity contact and each negative cavity contact is oriented symmetrically about the transverse plane, wherein each said battery pod is the same and capable of being releasably retained in any one of the cavities in said extension members.

10. The goggle of claim 6, further comprising a plurality of additional reserve battery pods capable of being stored on one of a user's body and a bandolier.

11. The goggle of claim 6, wherein the opposing cavities are molded into their respective extension members symmetrically such that a single type of battery pod may be used in each cavity on either extension member with battery pod contacts of each said battery pod connected with the contacts of each said battery cavity such that the battery contacts and the cavity contacts are located in a anterior portion of each said battery cavity that is closest to the goggle body.

12. The goggle of claim 11, wherein the wiring of the goggle is made to enable serial connection of the batteries where the cavity contact poles are symmetrically reversed in polarity relative to each other about a transverse plane through said goggle body to enable use of a single type of pod in symmetrical fashion about the transverse plane and in each inwardly-opening cavity in each said extension member.

13. The goggle of claim 6, further comprising a charger and wherein said batteries are rechargeable while in said battery pods.

14. The goggle of claim 6, further comprising a charging port adapted for plugging the goggle into a standard AC wall socket to enable charging of said batteries of the goggle.

15. The goggle of claim 12, wherein each said battery pod further comprises integrated means protecting against short circuit, over-voltage from said charger, under-voltage from said charger, over-temperature and current limitation circuitry.

16. The goggle of claim 6, wherein each said battery pod and cavity further comprises a spring-biased, thumb-releasable, tongue-and-groove interconnection means for securely, but releasably, interconnecting each said battery pod in a cavity.

* * * * *